United States Patent [19]
Addey et al.

[11] Patent Number: 5,721,342
[45] Date of Patent: Feb. 24, 1998

[54] CONTROL OF MILK SECRETION

[75] Inventors: Caroline Victoria Pauline Addey; Malcolm Peaker, both of Ayr; Colin James Wilde, Ayer, all of Scotland

[73] Assignee: British Technology Group Limited, London, England

[*] Notice: The term of this patent shall not extend beyond the expiration date of Pat. Nos. 5,496,802 and 5,502,163.

[21] Appl. No.: 477,661

[22] Filed: Jun. 7, 1995

Related U.S. Application Data

[63] Continuation of Ser. No. 150,558, Nov. 10, 1993, abandoned, which is a continuation of Ser. No. 857,917, filed as PCT/GB90/01742, Nov. 13, 1990 published as WO91/07434, May 30, 1991, abandoned.

[30] Foreign Application Priority Data

Nov. 13, 1989 [GB] United Kingdom ............... 8925594

[51] Int. Cl.⁶ .................... C07K 14/475; C07K 14/575; C07K 16/22; C07K 16/26
[52] U.S. Cl. ................... 530/832; 530/350; 530/388.24; 530/389.2; 530/833; 530/388.2; 530/395; 530/397; 530/399
[58] Field of Search ................ 424/130.1, 152.1, 424/156.1, 157.1, 145.1, 158.1; 435/240, 27, 70.21, 2, 332, 336; 514/2; 530/300, 328, 832, 387.1, 388.24, 389.2, 350, 833, 388.2, 399, 395, 397

[56] References Cited

U.S. PATENT DOCUMENTS 5,496,802  3/1996  Inude et al. ........................... 514/2
5,502,163  3/1996  Addey et al. ........................ 530/300

FOREIGN PATENT DOCUMENTS

94/26787  11/1994  WIPO.

OTHER PUBLICATIONS

Kalyan et al., "Role of carbohydrate in human chorionic gonadotropin", *J. Biol. Chem.*, 1983, 258, No. 1, 67–74.
Spiro, "Analysis of sugars found in glycoproteins", *Methods in Enzymology*, 1966, 8, 23–26.
Kornfeld et al., "Red kidney bean (*Phaseolus vulgaris*) phytohemagglutinin", *Methods in Enzymology*, 1972, 28, 344–349.
Anderson et al., "Isolation of a genomic clone for bovine pancreatic trypsin inhibitor by using a unique–sequence synthetic DNA probe", *Proc. Natl. Acad. Sci. USA*, 1983, 80, 6838–6842.
Kumagai et al., "Molecular cloning and sequencing of cDNA encoding goat pre–$\alpha$–Lactalbumin", *J.Biochem*, 1987, 101, No. 2, 511–517.
Lathe, "Synthetic oligonucleotide probes deduced from amino acid sequence data: theoretical and practical considerations", *J. Mol Biol*, 1985, 183, 1–12.
Sambrook et al., (eds.), "Molecular cloning. A laboratory manual.", *Cold Spring Harbor Laboratory Press*, 1989, 11.3–11.61.
Levy, "The effects of weaning and milk on mammary fatty acid synthesis", *Biochim. Biophys. Acta*, 1964, 84, 229–238.
Maule Walker et al., "Local production of prostaglandins in relation to mammary function at the onset of lactation in the goat", *J. Physiol.*, 1980, 309, 65–79.
Harlow and Lane (eds.), "Antibodies Manual", *Cold Spring Harbor Laboratory*, 1988, 173–176 and 195.
Mammary Gland Biology and Lactation Newsletter, vol. 8, No. 2, May 1989, pp. 1–4.
Suelter, "A Practical Guide to Enzmology", Wiley and Sons Pub, 1985, pp. 77–132.
Johnstone et al. "Immunochemistry in Practice", Blackwell Sci Pub., 1987, pp. 5–17, 148–182, 293–298.
Goding, Monoclonal Antibodies: Principles and Practice, Academic Press, 1986, pp. 281 and 282.
Goding, Production of monoclonal antibodies (Chapter 3) from "Monoclonal antibodies: Principles and Practice", Academic Press, 1986 pp. 59–103.
Prentice, A. et al, Biochem. Soc. Trans., 1989, 17(1), p. 122.
Wilde, C.J. et al, Biochem. J. 1987, 242(1), pp. 285–288.
Henderson, A.J. et al, J. Physiol. (London), 1984, 351, pp. 39–45.
Wilde, C.J. et al, Quart. J. Exp. Physiology, 1988, 73, pp. 391–397.
Wilde, C.J. et al, Biochem. Soc. Transactions, 1987, 15, pp. 916–917.

*Primary Examiner*—Ronald B. Schwadron
*Attorney, Agent, or Firm*—Nixon & Vanderhye

[57] ABSTRACT

A protein which inhibits milk secretion by lactating goats has been isolated from milk by anion exchange of a defined whey fraction, optionally followed by chromatofocussing, and is defined by reference to peaks in which it is found, its molecular weight of 7.6 KDa and pI of 4.8.

4 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 10 amino acids
    ( B ) TYPE: amino acid
    ( C ) STRANDEDNESS: unknown
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Ala  Gly  Pro  Phe  Xaa  Leu  Tyr  Xaa  Val  Asn
  1              5                        10

CONTROL OF MILK SECRETION

This is a Rule 62 continuation of application Ser. No. 08/150,558, filed 10 Nov. 1993, now abandoned, which is a continuation of U.S. application Ser. No. 07/857,917, filed Jul. 13, 1992, now abandoned, which a 371 of PCT/GB90/01742, filed Nov. 13, 1990.

BACKGROUND OF THE INVENTION

1. Field of the invention

This invention relates to a new protein isolated from goat's milk and the use of the protein or antibodies thereto for the control of milk secretion in lactating animals.

2. Description of the prior art

The rate of milk secretion by a lactating animal is regulated by the frequency of milk removal. In other words, there is a mechanism which acts to match the animal's supply of milk to the demand of her offspring or of a farmer's milking regime. Part of this control is achieved by the release of galactopoietic hormones during suckling or milking. However, studies by workers at the Hannah Research Institute, Ayr, Scotland on lactating goats have shown that another factor is involved. This is an inhibitor which decreases milk secretion at a local level, i.e. at the individual gland of an udder.

It has already been shown that the inhibitor is present in a goat milk fraction containing whey proteins of molecular weight 10–30 KDa, this range of molecular weights being determined by the nominal mesh sizes of filters used in ultrafiltration of the whey. The effect has been demonstrated both in vitro and in vivo. The in vitro technique, described by C. J. Wilde et al., Biochem. J. 242, 285–288 (1987), consists in culturing explanted pieces of rabbit mammary tissue with and without the milk fraction and demonstrating the inhibition of lactose and casein synthesis See also G. M. Stewart et al., J. Endocrinology 118, RJ-R3 (1988). In the in vivo technique, C. J. Wilde et al., Ouarterly Journal of Experimental Physiology 73, 391–397 (1988), the milk fraction was injected into a single mammary gland of goats via the teat canal. A temporary dose-dependent reduction of milk yield, specific to that gland, was observed. Other papers describing various other aspects of this research are C. J. Wilde et al., Biochem. Soc. Trans. 15, 916–917 (1988), C. J. Wilde et al., Biochem. Biophys. Acta., 992, 315–319 (1989), J. Mckinnon et al. J. Endocrinol 119 (supplement), 167 (1988) and M. Peaker and D. R. Blatchford, J. Dairy Res., 55, 41–48.

A brief report of a lecture given by Dr. C. J. Wilde to the International Society for Research in Human Milk and Lactation in New Orleans in March 1989 was published in the Mammary Gland Biology Newsletter (May 1989). The report said that the inhibitor had been, purified and its structure determined, but no details were given and the author of the report has since admitted that it was pure speculation without factual foundation.

It has therefore remained a problem to determine whether the goat milk inhibitor is a single compound or two or more compounds acting in concert, to isolate it or them from the 10–30 KDa fraction, and to purify it sufficiently for identification, with a view to chemical or biological synthesis.

SUMMARY OF THE INVENTION

It has now been found possible to separate the 10–30 KDa fraction by anion exchange chromatography into a number of peaks and it has been determined that the inhibitor activity is concentrated mainly in a particular peak which is not one of the most abundant. A protein has been isolated from this peak and its properties determined, and its activity as an inhibitor of milk secretion confirmed. Further, antibodies to the inhibitor have been found at least partly to neutralise the effect of the inhibitor.

Conventional ion-exchange chromatography using DEAE (diethylaminoethyl)-cellulose ion-exchange resin did not resolve the constituents of the 10–30 KDa fraction effectively. As a consequence, bioassay experiments on material eluted from this column gave equivocal results. Similarly, gel filtration of the 10–30 KDa fraction did not separate it effectively into individual components.

There are various ways of defining the protein of the invention, of varying degrees of reliability. One currently preferred definition is a protein which inhibits milk secretion by lactating goats and has (a) a molecular weight, as determined by gel filtration chromatography of the protein in its glycosylated form of about 7.6 KDa, (b) an N-terminal amino acid sequence (SEQ ID NO: 1) beginning

```
 1           5              1
Ala Gly Pro Phe Xaa Leu Tyr Xaa Val Asn
``` where Xaa are the same or different unknown amino acids, and (c) which is found in glycosylated form in goat's milk.

An alternative definition is a protein which inhibits milk secretion by lactating goats and which (d) (1) is the major protein present in the third significant peak when a nominally 10–30 kDa fraction of the whey proteins of the milk is resolved on an anion exchange column containing particles of monodisperse hydrophilic polymers having pendant —$CH_2N(CH_3)_3^+$ groups, the particle diameter being 10±0.5 µm, especially a "Mono Q" column, using 20 mM bis tris propane (1,3-bis[tris(hydroxymethyl)methylamino] propane) buffer, pH 7.0 and a sodium acetate gradient. This definition (d)(1) can optionally be supplemented. The supplementary definition (d)(2) provides that it is the major protein present in the second significant peak obtained when the said third peak of definition (d)(1) is resolved on a chromatofocussing column containing particles of monodisperse hydrophilic polymers having pendant tertiary (_$N^+HR_2$) and quaternary (_$N^+R_3$) amine groups, the Rs being organic substituents (not necessarily the same), the particle diameter being 10±0.5 µm, especially a "Mono P" column, using 0.025M piperazine-HCl, pH 5.5 and amphoteric buffer of pH 4.0, to create a pH gradient in the range 5.5–4.5.

Yet another possible definitive feature of the protein comprises (e) its approximate empirical amino acid composition as follows Asx 6, Thr 2, Ser 4, Glx 7, Pro 4, Gly 7, Ala 5, Val 1, Ile 2, Leu 4, Tyr 1, Phe 2, Lys 3, His 1, Arg 2, Met 5, Cys 1, Trp 0.

(Asx=Asn or Asp; Glx=Gln or Glu).

This composition is particularly rich in hydrophilic amino acids. The protein can be defined by features (b) and (e), alone or together with others.

Any combination of one or more of the features (a) to (e), together with the inhibitory action of the protein, might be sufficient to define the protein uniquely and accordingly applicant does not wish to be limited unnecessarily to combinations of all or nearly all of (a) to (e), in case one of them or some aspect of one of them might later be re-determined and found not sufficiently to approximate to their definition given above, while the remaining features are confirmed, and leave no doubt as to the identity of the protein. Precisely which features are the most meaningful and the most reliable are, in any case, a matter of judgement, the preferred definitions given above reflecting applicant's current judgement. It will be appreciated, therefore, that the protein defined by any combination of features herein set forth including, if desired, features deducible from the Examples, is to be considered as encompassed by the invention.

A property which might be useful for defining the protein is the isoelectric point (pI). It has been found that the third peak in definition d(1) gives a pI of about 4.8 to 4.9 in isoelectric focussing in a tube of polyacrylamide gel. However, the second peak in definition d(2) was eluted on chromatofocussing at an apparent pH 4.2.

The invention includes the inhibitor protein in glycosylated or unglycosylated form.

Antibodies to the protein, whether polyclonal, monoclonal or engineered, are within the scope of this invention.

Where national patent law permits, the administration of the inhibitor to decrease milk yield or an antibody thereto to suppress at least party the action of the inhibitor, to goats or other animals is within the invention.

DESCRIPTION OF THE PREFERRED EMBODIMENTS

Figure 1:
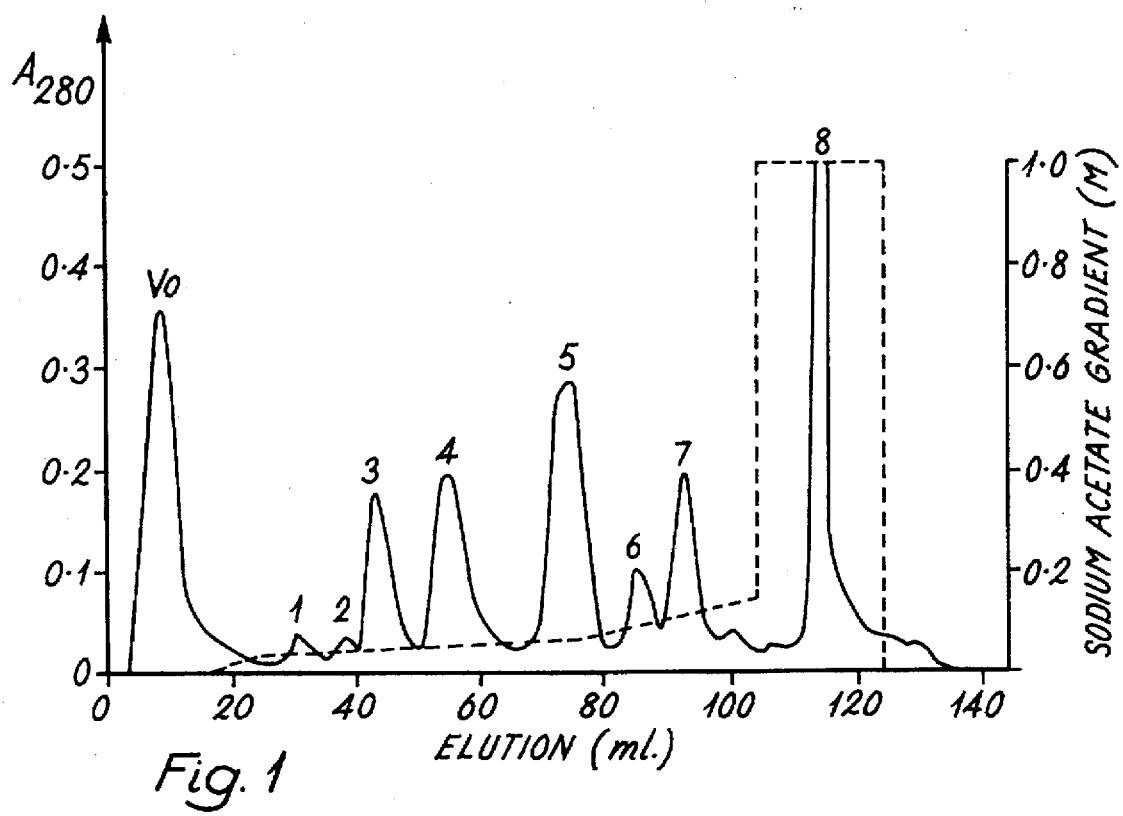
FIGS. 1 and 2 show the resolution of the 10–30 KDa fraction by an ion-exchange chromatography in two different buffers.

The protein of the invention exists in milk in glycosylated form. It is believed that the effect of glycosylation is simply for attachment of the protein to the appropriate cells within the mammary gland. It would be expected, therefore, that the protein could be administered locally to the gland in an unglycosylated form.

Using the 10–30 KDa fraction, it has been demonstrated that the inhibition of lactose and casein synthesis in mammary explant culture is dependent on the dose of the inhibitor-containing fraction. Further, when the explants have been exposed to the inhibitor-containing fraction, washed and re-cultured in fresh medium in the absence of the inhibitor, the capacity to synthesise lactose and casein is recovered. In vivo, it is found that administration of the protein to the mammary gland causes the milk yield to decrease within hours, with full recovery of yield 24–36 h after a single administration. However when a change in milking frequency—and therefore autocrine control—was sustained over weeks, there was an effect on the synthetic capacity i.e. degree of differentiation of the secretory cells attributable to the autocrine inhibitor. These long-term effects on mammary cell activity are accompanied by changes in the number of cell-surface hormone receptors for prolactin. Thrice-daily milking of lactating goats for 4 weeks increases cell differentiation and prolactin receptor number per cell, whereas a decrease in milking efficiency extending over 21 weeks reduces secretory cell differentiation and prolactin receptor number. Therefore, these long-term effects, and also the acute regulation by the autocrine inhibitor of the invention could be due primarily to modulation of the sensitivity of individual glands to endocrine control.

Antibodies can be raised against the protein of the invention by any conventional methods, e.g. as polyclonal antisera, muse monoclonal antibodies, or engineered antibodies made by recombinant techniques, by any of the currently available methods. Passive immunisation methods can then be used to generate a reduction in the effect of the natural inhibitor, when this is desired in order to increase milk yield. Frequently, however, there will be a need to reduce milk yield in order to meet milk quotas, in which event the inhibitor itself is administered. Conventional carriers and adjuvants known in vaccination can be used.

The invention is applicable to any animal responsive to the inhibitor defined herein. Since the 10–30 KDa goat milk fraction has been successfully found to reduce milk accumulation and relevant enzyme activities when injected into the mammary gland of rabbits, it is likely that the inhibitor will be effective in some other lactating animals.

A significant effect on goat milk yield was obtained by intraductal infection of an inhibitor fraction produced from 100 ml of milk. A significant unilateral effect on milk accumulation in rabbits was obtained by injecting 4 glands on one side each with 1.0–1.25 ml of 20 times concentration 10–30 KDa fraction i.e. from 20–25 ml of milk. At an estimated inhibitor concentration in milk of 0.1 µg/ml, this suggests that an effective intraductal dose in goats is 10 mg/gland. Effects can therefore be expected from injection in the range 1 to 50 µg especially 5 to 20 µg, of inhibitor.

This dose would be repeated as required, e.g. daily, and possibly reduced when given over long periods.

The protein of the invention can be obtained from goat's milk by the method described in Example 1 or some variant thereon. It can be recovered in pure form from an eluate by extensive dialysis against water (using an appropriate membrane for retention of the protein, e.g. with a nominal molecular weight cut-off of about 6 KDa) and freeze-drying. However, it is expected that it would be synthesised by protein synthesis or by a recombinant DNA method.

The following Examples illustrate the invention.

EXAMPLE 1

This Example describes the preparation and properties of the inhibitor of the invention.

1. Preparation of goat milk fractions

Milk was obtained at the morning milking from British Saanen goats in mid-lactation (except where indicated), and was defatted by centrifugation (2500 g, 15° C., 20 min) and filtered through glass wool. Defatted milk was dialysed against 40 volumes of 10 mM Hepes, pH 7.4, using SPECTROPOR™ 1 dialysis membrane (molecular weight cut-off 6000–8000 Daltons), or centrifuged (80,000 g, 15° C., 2 h), yielding a pellet of casein micelles and a clear supernatant containing whey proteins.

Portions of the whey protein fraction were subjected to ultrafiltration using filters with nominal cut-off values of molecular weight 10,000, 30,000, 50,000 and 300,000 Daltons (Da). In each case, the retentate volume was decreased by 95% and washed with 4 volumes of 10 mM Hepes, pH 7.4. The filtrate containing material of m.w. less than 10,000 Da was concentrated by freeze-drying. Other filtrates, and the retentate obtained with the 30,000 Da filter, were concentrated by ultrafiltration with a 10,000 Da filter. Fractions were sterilized by gamma-irradiation or by filter sterilization. The 10,000–30,000 Da fraction was dialysed exhaustively against distilled water and concentrated by freeze-drying for anion exchange chromatography.

2. Anion exchange chromatography of goat whey proteins

The 10–30 KDa whey fraction was resolved on a "MONO Q™ HR 10/10" anion exchange column (Pharmacia) using FPLC (Fast Protein Liquid Chromatography). MONO Q™ is a strong anion exchanger based on Mono Beads—monodisperse hydrophilic polymer particles (10±0.5 μm diamter) which bind negatively-charged components through quaternary amine groups [—$CH_2N(CH_3)_3^+$]. Two buffer systems were used:

(a) 20 mM bis tris propane (1,3-bis [tris(hydroxymethyl) methylamino]propane), pH 7.0, using a sodium acetate gradient to elute individual proteins; this buffer system was used to prepare proteins for bioassay experiments (FIG. 1).

(b) 10 mM imidazole, pH 7.0, using an elution gradient of sodium chloride (FIG. 2); this buffer system produced a similar separation, but with sharper peaks than (a).

The whey fraction was dissolved in the appropriate starting buffer (20 mM his tris propane or 10 mM imidazole) at twice its concentration in the original milk and solutions were adjusted to pH 7.0. Before chromatography, the sample and buffers were filtered through 0.2 μm filters. In addition, buffers were degassed before use. 2 ml of the 2× concentrated whey fraction was loaded for each separation; the flow rate was 4.0 ml/min.

Fractions containing protein peaks eluted from the column were dialysed extensively against distilled water, freeze-dried and stored at −20° C., before use in the next stage.

FIG. 1 of the drawings shows the elution of protein from the chromatography column. Protein concentration, as absorption of light at 280 nm, on the left-hand ordinate is plotted by a solid line against cumulative volume of eluted material on the abscissa. The right-hand ordinate is calibrated to show the sodium acetate gradient, from 0 to 1.0M, used in the eluant (a), and the gradient is plotted by a broken line. The peaks are labelled Vo=void volume containing material not bound to the column and then 1–8 in order of elution.

Figure 2:
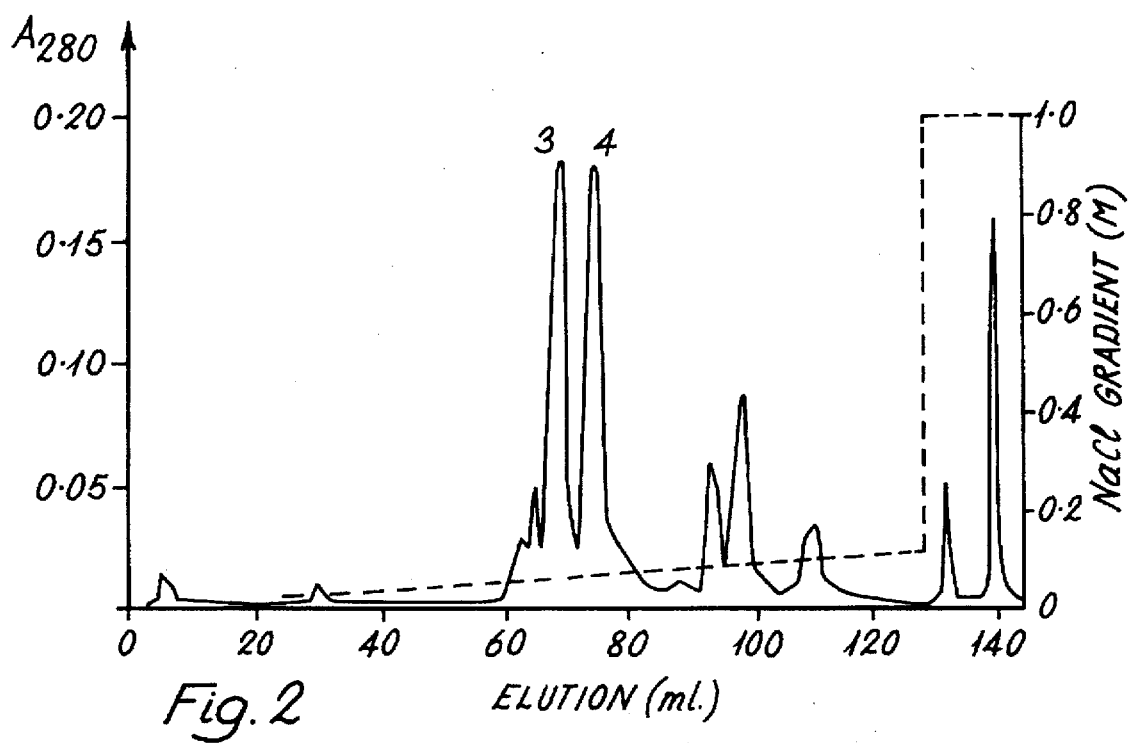

FIG. 2 of the Drawings is a similar plot to FIG. 1, but for the imidazole buffer system, the right-hand ordinate being calibrated in 0–1.0M sodium chloride gradient. The two central peaks at elution volumes of 65–80 ml. are believed to correspond to Nos. 3 and 4, respectively, of FIG. 1.

FIGS. 1 and 2 relate to typical chromatographies, but the relative sizes of the peaks vary from one preparation to another.

3. Mammary explant bioassay of goat milk fractions

Mammary tissue was cultured as explants, small pieces of parenchymal tissue approximately 1 cm³ and weighing 0.5–0.7 mg. Explants were prepared from mammary tissue of mid-pregnant New Zealand White rabbits as described by R. Dils & I. A. Forsyth in Methods in Enzymology 72, 724–742 (1981). The explants were cultured in a defined culture medium (Medium 199; Gibco Europe Ltd., Paisley, UK) on stainless steel grids each holding 30 explants, so that the explants were in contact with the medium but not completely submerged in it. The medium was supplemented throughout with insulin (5 μg/ml), cortisol (100 ng/ml) and prolactin (1 μg/ml). Explants were cultured in this medium under an atmosphere of air/$CO_2$ (19:1 v/v) for 42 h, with replenishment of medium after 24 h. At this time, groups of explants (3 or 4 groups per treatment) were transferred into fresh medium containing hormones and one of the fractions of goat milk obtained by anion exchange chromatography as described above. The milk fractions were dissolved in 10 mM Hepes, pH 7.4, at twice their concentration in the original milk, and added to an equal volume of two times concentrated culture medium, so as to be at 100% of their original milk concentration in normal strength culture medium. Control cultures, containing only the diluent for the milk fractions, were included in each experiment. Average rates of lactose and casein synthesis during a further 6 h culture in the presence or absence of milk fraction were measured by the addition of [U-$^{14}$C]glucose (U=uniformly labelled; 0.18 mCi/mmol) and L-[4,5-$^3$H]leucine (2.22 mCi/mmol) respectively to this culture medium. At the end of the −6 h period, explants and culture medium were separated and stored frozen in liquid nitrogen.

Explants were homogenized at 4° C. in 1.0 ml of 10 mM Tris/HCl, pH 7.0, containing 5 mM ethyleneglycol-bis-(2-aminoethyl ether) N,N,N',N'-tetraacetic acid (EGTA) and 2 mM phenylmethane-sulphonyl fluoride by 10 strokes with a glass/PTFE homogenizer, followed by sonication for 30 s (Kontes ultrasonic cell disruptor, 30% maximum power), and a particle-free supernatant was prepared by centrifugation at 10,000 g for 5 min. [$^3$H]-labelled casein was prepared from the particle-free supernatant by precipitation at its isoelectric point, and the precipitate was subjected to SDS-polyacrylamide gel electrophoresis, as described by C. J. Wilde et al., Exp. Cell Res. 151, 519–532 (1984). Bands corresponding to casein polypeptides were visualized by staining with COOMASSIE™ brilliant blue, and were excised and counted for [$^3$H] radioactivity as described by S. N. Russell et al., Biochim. Biophys. Acta 714, 34–45 (1982). [$^{14}$C] lactose was selectively precipitated from explant homogenates and culture medium using ethanol/diethyl ether (3:1, v/v), N. J. Kuhn & A. White, Biochem. J. 148, 77–84 (1975) and the radioactivity of the precipitate counted. Results were corrected for carry-through of [$^{14}$C] glucose from culture medium (usually <0.08%), by measuring [$^{14}$C] radioactivity after extraction of uncultured medium. The addition of milk fractions did not affect the distribution of secreted products between the extracellular space of the explants and the medium.

The amount of radioactive material (casein and lactose) was expressed as a percentage of that produced by the explants to which no milk fraction had been added. The results are shown in Table 1. Numbers of determinations are shown in parenthesis.

TABLE 1

| Fraction | Lactose synthesis % inhibition | Casein synthesis % inhibition |
| --- | --- | --- |
| Unfractionated | 29.5 ± 5.6 (13)* | 32.2 ± 5.2** |
| Void volume | 6.2 ± 7.7 (9) | 7.9 ± 8.7 |
| Peaks 1 + 2 | 1.0 ± 15.6 (5) | 13.1 ± 9.6 |
| Peak 3 | 31.5 ± 7.2 (13)* | 35.1 ± 3.6*** |
| Peak 4 | 30.1 ± 7.7 (7) | 7.2 ± 10.2 |
| Peak 5 | 10.8 ± 20.6 (11) | 17.7 ± 7.6 |
| Peak 6 | 5.5 ± 5.2 (10) | 6.3 ± 8.3 |
| Peak 7 | 14.2 ± 8.4 (5) | 1.0 ± 8.0 |
| Peak 8 | 23.4 ± 10.5 (3) | (13.9 ± 7.9§) |

TABLE 1-continued

| Fraction | Lactose synthesis % inhibition | Casein synthesis % inhibition |
| --- | --- | --- |

§Stimulation, i.e. casein synthesis apparently exceeded that of the control in which no milk was added. Peak 8 contained a lot of protein (not resolved by the gradient) which, in the 3 experiments in which it was tested, may have had non-specific effects on the explants.
*$p < 0.05$;
**$p < 0.01$;
***$p < 0.001$ From Table 1 it will be seen that peaks 3 and 4 were the most active in inhibiting lactose synthesis. Lactose synthesis is a major determinant of milk yield.

4. Gel filtration chromatography of peak 3

Gel filtration of peak 3 was carried out using an "FPLC" chromatography system and a Superose 12 HR 10/30 column (Pharmacia). The buffer was 50 mM Tris/HCl, pH 7.5 containing 100 mM KCl, which was filtered (0.2 µm filter) and degassed before use. Samples (routinely 1–10 µg in a maximum volume of 200 µl) were dissolved in the same buffer and filtered before use (0.2 µm filter). The column was calibrated using molecular weight standards in the m.w. range 200,000–12,400 (Sigma MW-GF-200 kit) and also aprotinin (molecular weight 6,500) and bovine α-lactalbumin (molecular weight 14,200). Calibration curves of log[molecular weight] versus $V_e/V_o$ were prepared, where $V_o$=void volume and $V_e$=elution volume of each protein $V_o$ was determined using Dextran Blue (Sigma; approximate molecular weight 2,000 KDa). The molecular weight of peak 3 protein was thus determined to be about 7.6 KDa. (An attempt at m.w. determination by SDS-PAGE gave anomalous results: it appears that high molecular weight aggregates form). The unexpectedly low molecular weight can probably be explained by clogging of the nominally 10,000 Dalton filter during ultrafiltration, allowing smaller molecules to be retained.

5. Assessment of Protein Glycosylation

Hexose determination of the peak 3 protein separated by gel filtration chromatography was by the "Anthrone" method as described by R. G. Spiro, Methods in Enzymology, 8, 4–5 (1966). By this method, peak protein contained 70 µg hexose per 100 µg protein) (average of 2 determinations), indicating glycosylation. Control unglycosylated proteins (bovine α-lactalbumin and RNase A) contained negligible amounts of hexose under the assay conditions.

6. Isoelectric focussing of goat whey proteins

Isoelectric focussing was performed in tube gels (diameter, 4 mm; length 11.5 cm). 4% polyacrylamide gels were prepared essentially as described by P. H. O'Farrell J. Biol. Chem. 250, 4007–4021 (1975) using a mixture of ampholines (4% v/v pH range 5–8; 1% v/v pH range 3.5–10; BioRad), which gave a linear gradient in the range 4.0–9.0. Samples (25 µg of the peak 3 protein) were dissolved in a solution containing 9.5M urea, 2% (w/v) NP40, 1.6% (v/v) pH 5–8 ampholines and 0.4% (v/v) pH 3.5–10 ampholines. The anodic and cathodic solutions were 10 mM $H_3PO_4$ and 20 mM NaOH respectively. Electrophoresis was at 300 V for 18 h, followed by 400 V for 4 h. Gels were extruded and fixed first in 25% (v/v) isopropanol/10% (v/v) acetic acid, then in 5% (w/v) TCA/5% (w/v) sulphosalicylic acid/1% (v/v) methanol, and were stained 25% (v/v) isopropanol/10% (v/v) acetic acid containing 0.1% (w/v) COOMASSIE™ Blue. Destaining was in isopropanol/acetic acid.

The isoelectric point of the peak 3 protein was thus found to be 4.85.

7. Amino acids

Amino acid composition was determined and the empirical ratio of amino acids in the peak 3 was calculated using Arginine=2 as the standard value. Results are shown in Table 2.

TABLE 2

| Amino acid | Net amount (nmoles) | Amino acid ratio |
| --- | --- | --- |
| Asx (Asp or Asn) | 6.937 | 6 |
| Thr | 2.587 | 2 |
| Ser | 5.439 | 4 |
| Glx (Gln or Glu) | 9.173 | 7 |
| Pro | 4.404 | 4 |
| Gly | 8.181 | 7 |
| Ala | 6.204 | 5 |
| Val | >>standard, amount unknown | 1 |
| Ile | 1.398 | 2 |
| Leu | 4.604 | 4 |
| Tyr | 0.752 | 1 |
| Phe | 2.178 | 2 |
| Lys | 3.762 | 3 |
| His | 1.138 | 1 |
| Arg | 2.466 | 2 |
| Met | 5.747 | 5 |
| Cys | 1.398 | 1 |
| Trp | — | 0 |

The molecular weight calculated from the above empirical amino acid composition data was 7136. This is consistent with the m.w. 7600 obtained by gel permeation chromatography of the glycosylated protein, the difference being accountable for by glycosylation.

N-terminal amino acid sequencing of the first 10 amino acids gave SEQ ID NO: 1 in which the unknown fifth amino acid is possibly Val and the eighth amino acid is possibly Glu.

8. Catalysis of Lactose Synthesis

Peak 3 does not promote the synthesis of lactose by galactosyltransferase. This indicates that it is not related to α-lactalbumin, the principal whey protein. Lactose synthetase activity is associated with peaks 5 to 7, indicating that these peaks contain the several forms of α-lactalbumin in goat milk.

9. Other properties of peak 3

(a) Hydrophilicity

Reversed phase chromatography of peak 3 indicated that it is strongly hydrophilic.

(b) Spectral Analysis

The peak 3 protein absorbs maximally at 261 nm. The calculated molar extinction coefficient for absorption at 280 nm is $5.12 \times 10^8$. This absorbance is high compared with other whey proteins, which indicates that peak 3 constitutes only a small proportion of the 10–30 KDa fraction.

(c) Stability

The peak 3 protein, purified by gel filtration chromatography, was stored for 2 weeks as a lyophilized powder at −20° C., or in solution in 10 mM Hepes buffer pH 7.0 at 37° C. When re-analysed by the same gel filtration chromatography technique, there was no evidence of either a decrease in protein content of the peak, or the appearance of low molecular degradation products. Therefore, the protein appears to be stable in the conditions under which it has been prepared and tested.

10. Separation of peak 3 components by chromatofocussing

Chromatofocussing separates proteins on the basis of their isoelectric point (pI). Resolution with the Pharmacia "MONO P™ HR 5/20" column is such that molecules differing in pI by only 0.02 pH units can be separated "Mono P" is a weak anion exchanger, based on mono beads, i.e. monodisperse hydrophilic polymer particles (10±0.5 μm diameter) into which various tertiary ($-N^+HR_2$) and quaternary ($-N^+R_3$) amine groups are introduced. "MONO P™" has a buffering capacity and the amount of charge it carries will vary with pH. Consequently, its ionic capacity will also vary with pH. In chromatofocussing, a pH gradient is formed on the column by equilibrating it with start buffer and eluting with another buffer which is added in increasing amounts, thereby adjusting the solution progressively to a lower pH. Proteins bound to the column at the starting pH are eluted at different points on the pH gradient according to their pI.

A "MONO P™" column was first equilibrated with 0.025M piperazine-HCl pH 5.5, and a pH gradient (5.5–4.0) was formed in situ in the column by elution with "POLYBUFFER™74", pH 4.0 (diluted 1/10 in distilled water). "Polybuffer" (Pharmacia) contains numerous amphoteric buffering substances of different pKa. Buffers were filtered through 0.2 μm filters and degassed before use. The flow rate was 0.75 ml/min. Samples (peak 2, 3, & 4 from the anion exchange column) were dissolved at approximately 50–100 μg in 1.0 ml of 0.025M piperazine-HCl pH 5.5 and filtered through 0.2M filters. Fractions containing protein peaks were collected, dialysed extensively against distilled water, freeze-dried and stored at −20° C.

Figure 4:
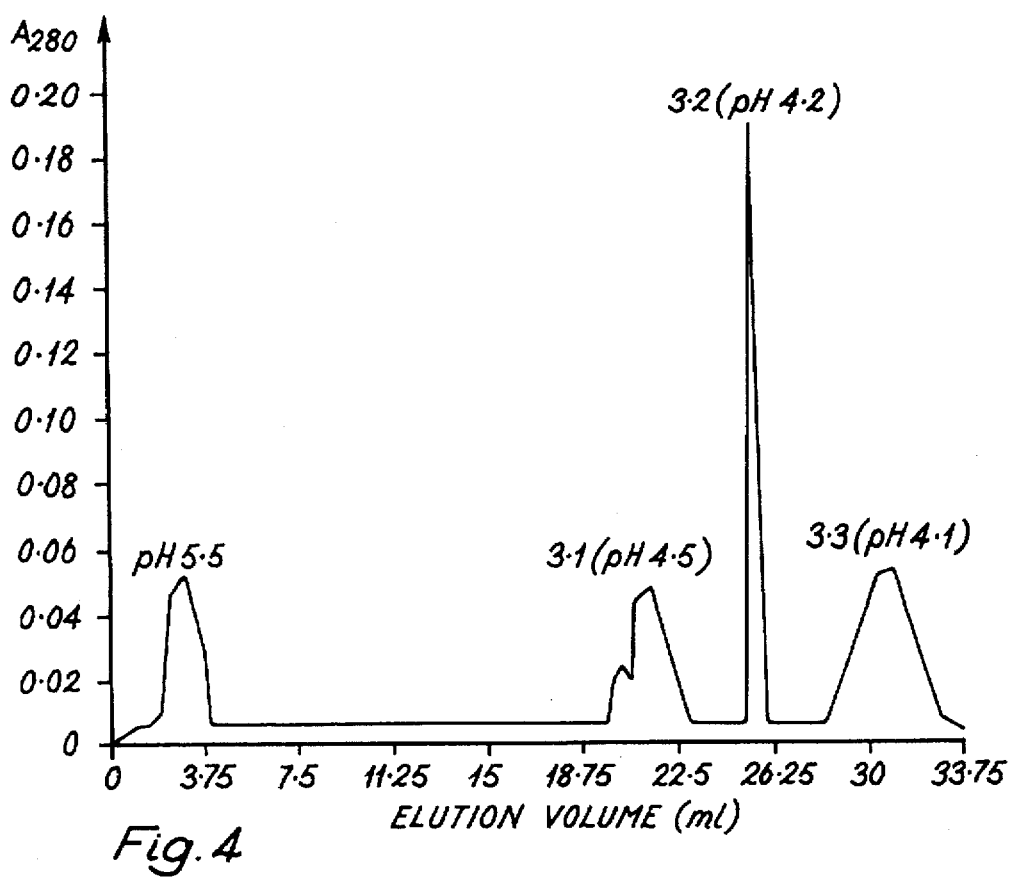
FIG. 4 shows the resolution by chromatofocussing of three protein peaks obtained by anion exchange chromatography.

FIG. 4 of the drawings shows the elution profile obtained using peak 3. Protein concentration, as absorption of light at 280 nm, on the left hand ordinate is plotted by a solid line against cumulative volume of eluted material on the abscissa. Peak 3 contained three major components labelled 3.1, 3.2 and 3.3. The apparent pHs were estimated using Whatman indicator papers (type CS, pH 3.8–5.5) and may not reflect accurate pI values. Each peak did however elute consistently at the same cumulative volume. FIG. 4 shows a typical elution profile, but the relative sizes of the peaks may vary from one preparation to another.

Anion exchange peaks 2 and 4 each contained three components, designated 2.1, 2.2, 2.3 and 4.1, 4.2, 4.3. Comparison of all three profiles suggested that 3.1 arises by contamination with 2.1; 3.2, the major component of peak 3, is also a "contaminant" of peak 4 (i.e. 4.2); 3.3 may arise through contamination with 4.3, the major constituent of peak 4. Peaks 2.2 and 2.3 elute at positions which do not correspond to 3.2 or 3.3

11. Mammary explant bioassay of peak 3.2

The procedure of Section 3 was repeated on the chromatofocussed fractions from peak 3, except that they were added to bioassay culture medium to give a final concentration of three times their concentration in the original milk. The results are shown in Table 2. Numbers of determinations are shown in parenthesis.

TABLE 2

| Fraction | Lactose synthesis % inhibition | Casein synthesis % inhibition |
|---|---|---|
| 3.1 | 4.5 ± 30.1 (4) | 6.0 ± 9.8 |
| 3.2 | 19.6 ± 16.9 (4) | 32.2 ± 12.6 |
| 3.3 | (13.7 ± 28.8 (4)§) | (12.5 ± 8.70 §) |

§ Stimulation, i.e. lactose or casein synthesis apparently exceeded that of the control in which no milk was added.

The results of Table 2 suggest that inhibitory activity is most consistently associated with the major peak 3.2.

12. Gel Filtration of chromatofocussed peaks

Section 4 was repeated on the fractions 3.1, 3.2 and 3.3, the chromatofocussed peaks, obtained in Section 10. They all eluted at a similar position implying molecular weights of about 7600 Da.

EXAMPLE 2

This Example illustrates the preparation of antibodies to the inhibitor and their use in detecting the inhibitor and their ability to block the inhibition of the synthesis of lactose and casein.

To prepare rabbit anti-(goat peak 3 protein) for use in an ELISA, the peak 3 was dissolved in 0.5 ml of phosphate-buffered saline, pH 7.6, and administered as an emulsion with Complete Freund's adjuvant. Female New Zealand White Rabbits were given a primary subcutaneous injection of 100 μg protein at multiple sites along the back. 28 days later, a second subcutaneous injection was given as above but using Incomplete Freund's adjuvant. Rabbits were bled 7 and 14 days later from the marginal ear vein, by making a small cut with a sterile scalpel blade.

ELISA plates (Flow Laboratories) were coated with 1–5 μg of individual peaks 3, 4, 5, 6 and 7 prepared from the 10–30 KDa whey fraction, each dissolved in 100 μl of phosphate-buffered saline (PBS). After incubation overnight at 4° C., the plates were washed 3 times with PBS and 0.1% "TWEEN™20". 150 μl of PBS, 0.1% "TWEEN™20" and 5% BSA were added to each well and the plates were stood for 1 h at room temperature, to allow saturation of non specific binding sites. Plates were washed 3 times as above and 100 μl of the rabbit anti-(goat peak 3 protein) antiserum (diluted 1:200 in PBS) was added to each well. After 2 h at 40° C., the plates were again washed and 100 μl of peroxidase-linked anti-rabbit IgG antiserum (Scottish Antibody Production Unit) diluted 1:1000 in PBS+0.1% "TWEEN™20" 0.5% BSA were added. The plates were incubated again for 2 h at 4° C. They were then washed 5 times as above and 100 μl of ortho-phenylene diamine (OPD) substrate (0.4 mg/ml OPD in 11.38 mM $Na_2HPO_4$ and 46.45 mM citric acid pH 6.0 containing 0.01% $H_2O_2$) was added to each well. Colour was allowed to develop in the dark for 20 min, and the reaction was terminated by the addition of 50 μl 4M $H_2SO_4$. Absorbances were read at 492 nm using a MULTISCAN™ microtitre reader (Flow). Antibody only and antigen only control values were subtracted from each test reading.

Figure 3:
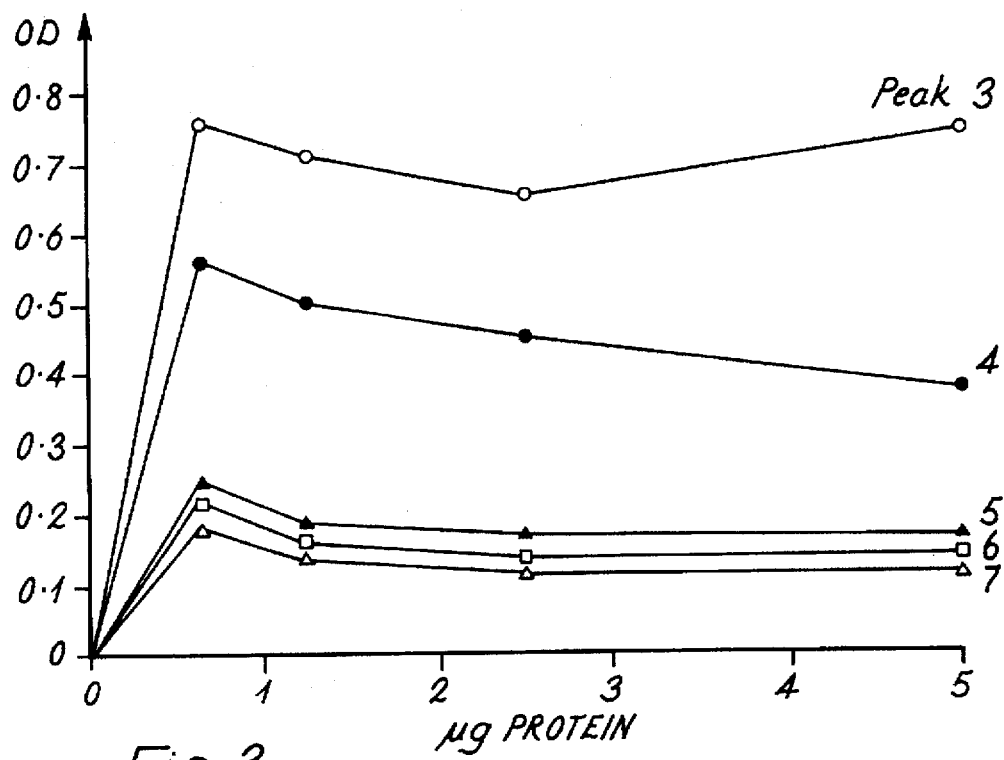
FIG. 3 shows the results of an ELISA in which samples from various peaks of the FIG. 1 chromatography are tested for ability to bind to antiserum raised against the peak containing the protein of the invention.

The results are shown graphically in FIG. 3 in which units of optical density are plotted on the ordinate against amounts of the peak material on the abscissa. Each value represents the average of two determinations. It will be seen that the antibody binds strongly to the peak 3 material, as expected but that there is some cross-reactivity with peak 4.

Results of two bioassay experiments showed that inhibition of lactose and casein synthesis by the inhibitor was partially reversed when the above antiserum was included (at an arbitrary concentration) in the culture medium. Lactose synthesis was inhibited by 19% when no antibody was added, but by 9% with the antibody present. Casein synthesis inhibition was inhibited by 39% when no antibody was added, but by 21% when it was present. Rabbit control serum had no effect on the inhibition of lactose synthesis, and only slightly reversed the inhibition of casein synthesis.

a 0 to 1.0M sodium acetate gradient, and which is further defined as the major protein present in the second significant peak obtained when said third peak is resolved on a chromatofocussing column containing particles of monodisperse hydrophilic polymers having pendant tertiary ($\_N^+HR_2$) and quaternary ($\_N^+R_3$) amine groups, the Rs being organic substituents, the particle diameter being 10±0.5 μM, using

---

---

We claim:

1. An isolated protein in glycosylated form, which inhibits milk secretion by lactating goats and which is the major protein present in the third significant peak when a fraction of the whey proteins of the milk, separated by ultrafiltration using filters of cut-off values 10 KDa and 30 KDa, is resolved on an anion exchange column containing particles of monodisperse hydrophilic polymers having pendant —$CH_2N(CH_3)_3^+$ groups, the particle diameter being 10±0.5 μm using 20 mM bis tris propane buffer, pH 7.0 and a 0 to 1.0M sodium acetate gradient, and which is further defined as the major protein present in the second significant peak obtained when said third peak is resolved on a chromatofocussing column containing particles of monodisperse hydrophilic polymers having pendant tertiary ($\_N^+HR_2$) and quaternary ($\_N^+R_3$) amine groups, the Rs being organic substituents, the particle diameter being 10±0.5 μM, using 0.025M piperazine-HCl, pH 5.5 and amphoteric buffer of pH 4.0 to create a pH gradient of 5.5–4.5 and which protein also possesses a molecular weight, as determined by gel filtration chromatography of material from said third peak, of about 7.6 KDa and an isoelectric point, as determined by isoelectric focussing of material from said third peak in a tube of polyacrylamide gel, of 4.8 to 4.9, or an unglycosylated form thereof.

2. Antibody to an isolated protein in glycosylated form, which inhibits milk secretion by lactating goats and which is the major protein present in the third significant peak when a fraction of the whey proteins of the milk, separated by ultrafiltration using filters of cut-off values 10 KDa and 30 KDa, is resolved on an anion exchange column containing particles of monodisperse hydrophilic polymers having pendant —$CH_2N(CH_3)_3^+$ groups, the particle diameter being 10±0.5 μm using 20 mM bis tris propane buffer, pH 7.0 and a 0 to 1.0M sodium acetate gradient, and which is further defined as the major protein present in the second significant peak obtained when said third peak is resolved on a chromatofocussing column containing particles of monodisperse hydrophilic polymers having pendant tertiary ($\_N^+HR_2$) and quaternary ($\_N^+R_3$) amine groups, the Rs being organic substituents, the particle diameter being 10±0.5 μM, using 0.025M piperazine-HCl, pH 5.5 and amphoteric buffer of pH 4.0 to create a pH gradient of 5.5–4.5 and which protein also possesses a molecular weight, as determined by gel filtration chromatography of material from said third peak, of about 7.6 KDa and an isoelectric point as determined by isoelectric focussing of material from said third peak in a tube of polyacrylamide gel, of 4.8 to 4.9, or to an unglycosylated form thereof.

3. An isolated protein which inhibits milk secretion by lactating goats and which is the major protein present in the third significant peak when a fraction of the whey proteins of the milk, separated by ultrafiltration using filters of cut-off valves 10 KDa and 30 KDa, is resolved on an anion exchange column containing particles of monodisperse hydrophilic polymers having pendent $CH_2N(CH_3)_3^+$ groups, the particle diameter being 10±0.5 μm using 20 mM his tris propane buffer, pH 7.0 and a 0 to 1.0M sodium acetate gradient, and which is further defined as the major protein present in the second significant peak obtained when said third peak is resolved on a chromatofocussing column containing particles of monodisperse hydrophilic polymers having pendant tertiary ($\_N^+HR_2$) and quaternary ($\_N^+R_3$) amine groups, the R's being organic substituents, the particle diameter being 10±0.5 μM, using 0.025M piperazine-HCl, pH 5.5 and amphoteric buffer of pH 4.0 to create a pH gradient of 5.5–4.5 and which protein also possesses a molecular weight, as determined by gel filtration chromatography of material from said third peak, of about 7.6 KDa and an isoelectric point, as determined by isoelectric focussing of material from said third peak in a tube of polyacrylamide gel, of 4.8 to 4.9.

4. Antibody to the isolated protein claimed in claim 3.

* * * * *